(12) United States Patent
Sato et al.

(10) Patent No.: US 7,186,858 B2
(45) Date of Patent: Mar. 6, 2007

(54) METHOD FOR PRODUCING CARBOXYLIC ACID

(75) Inventors: Kazuhiko Sato, Ibaraki (JP); Youko Usui, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 247 days.

(21) Appl. No.: 10/522,367

(22) PCT Filed: Jul. 24, 2003

(86) PCT No.: PCT/JP03/09376

§ 371 (c)(1),
(2), (4) Date: Jan. 25, 2005

(87) PCT Pub. No.: WO2004/011412

PCT Pub. Date: Feb. 5, 2004

(65) Prior Publication Data

US 2005/0215817 A1    Sep. 29, 2005

(30) Foreign Application Priority Data

Jul. 25, 2002  (JP) .............................. 2002-216692
Jul. 25, 2002  (JP) .............................. 2002-216841

(51) Int. Cl.
*C07C 51/00*  (2006.01)
(52) U.S. Cl. ...................... 562/528; 562/497
(58) Field of Classification Search ...................... None
See application file for complete search history.

(56) References Cited

FOREIGN PATENT DOCUMENTS

JP         43-19286 B      8/1968
JP         54-135720 A    10/1979

OTHER PUBLICATIONS

Zhang Shi-gang, et al, "Geen Catalytic Oxidation of Cyclohexanone to Adipic Acid.", 2002, Science & Technology in Chemical Industry, vol. 10, No. 5, pp. 4 to 6, 16.
Xian-miao Long et al., "Green synthesis of adipic acid by catalytic oxidation of cyclohexanol/cyclohexanone," Huagong Keji (2002), 10(5), pp. 4-6, 16.
Kenji Nomiya et al., "Catalysis by heteropolyacid-VII. Catalytic Oxidation of Cyclohexanol by dodecamolybdate," *Polyhedron*, vol. 3, No. 5, pp. 607-610, 1984.
Yasutaka Ishii et al., "Hydrogen peroxide of cyclohexanone and cyclohexanone peroxide in the presence of some metal oxides," *Chemistry Letters*, vol. 6, pp. 611-614, 1978.
Yoko Usui et al., "A green method of adipic acid synthesis: organic solvent- and halide-free oxidation of cycloalkanones with 30% hydrogen peroxide," *Green Chemistry*, vol. 5, pp. 373-375, 2003.
Shi-gang Zhang et al., "Green catalytic oxidation of cyclohexanone to adipic acid," *Petroleum Science and Technology*, vol. 21, Nos. 1 & 2, pp. 275-282, 2003.

*Primary Examiner*—Sikarl A. Witherspoon
(74) *Attorney, Agent, or Firm*—Morgan, Lewis & Bockius LLP

(57) ABSTRACT

The present invention provides a safe, convenient and efficient method for producing carboxylic acid by a reaction of alicyclic alcohol with an aqueous hydrogen peroxide to thereby obtain carboxylic acid in high yield from alicyclic alcohol or alicyclic ketone under mild reaction conditions, wherein the reaction operation is simple and easy, a step for removing solvent after completion of the reaction is not necessary and influence and toxicity upon the environment and human body are markedly small. In order to provide it, an oily alicyclic alcohol is allowed to react with an aqueous hydrogen peroxide in the presence of a catalyst containing a metal compound belonging to Group 6 of the Periodic Table in a heterogeneous solution system.

5 Claims, No Drawings

US 7,186,858 B2

METHOD FOR PRODUCING CARBOXYLIC ACID

TECHNICAL FIELD

The present invention relates to a method for producing carboxylic acid as important intermediates in syntheses of diesters, polyesters and polyamides which are useful substances broadly used in various industrial fields, including chemical industry, as plasticizers, lubricants, heating media, dielectric media, fibers, copolymers, paints, surfactants, fungicides, insecticides, adhesives, and the like. More particularly, it relates to a novel method for producing carboxylic acid by a reaction of alicyclic alcohol or alicyclic ketone with an aqueous hydrogen peroxide.

BACKGROUND OF THE INVENTION

Methods for producing carboxylic acid by oxidation of alcohol with nitric acid (*Org. Synth.*, 5, 9–11, *Org Synth.*, Coll. Vol. 1, 18–20, *Compt. Rend.*, 1919, 168, 1324–1326, *J. Chem. Soc.*, 1942, 559–562, *J. Chem. Soc., Perkin Trans. II*, 1985, 1677–1682), chromic acid (*Org. Synth.*, Coll. Vol. 4, 19–21), potassium permanganate (*Chem. Ber.*, 1908, 41, 575, *Chem. Ber.*, 1922, 55B, 3526–3536) have been reported. However, it is hard to say that these methods are industrially superior processes because of the large load on the environment in terms of the generation of by-products having high toxicity, corrosiveness of the oxidizing agents, and the like.

On the other hand, oxygen and hydrogen peroxide are excellent oxidizing agents in industrially applying them due to small environmental load, because they are inexpensive and have no corrosiveness, and there is no by-product after the reaction or it is harmless water.

As a method for producing carboxylic acid from alcohol by using oxygen as the oxidizing agent, a method using a platinum-supported catalyst has been already proposed (*Appl. Cat. A*, 1996, 135, L7-L11).

However, this method must be carried out under pressurization of oxygen at a high reaction temperature (150° C. or more) and, in addition, selectivity of the obtained carboxylic acid is as low as merely about 50%.

On the other hand, methods for obtaining carboxylic acid by using hydrogen peroxide as the oxidizing agent include a method in which a homogeneous solution of cyclohexanol and hydrogen peroxide is prepared in advance by using a polar solvent, and adipic acid is produced by allowing this homogeneous solution to react in the presence of a catalyst such as a metal oxide belonging to Group 6 of the Periodic Table has been proposed (JP-A-54-135720).

However, it cannot be said yet that this method is sufficient as an industrial carboxylic acid production method, because the yield of adipic acid by the method is considered to be merely about 50%, and it is essential to use a polar solvent such as acetic acid or t-butyl alcohol for preparing a homogeneous solution by dissolving cyclohexanol in an aqueous hydrogen peroxide, so that the reaction operation and apparatus become complex because of the necessity to employ a means for its removal at the time of the isolation of adipic acid as the product of interest, in addition to the indication on the influence and toxicity of the polar organic solvent itself upon the environment and human body.

In addition, in the method for producing carboxylic acid by oxidation of ketone, nitric acid is used as the oxidizing agent (*Chem. Ber.*, 1894, 27, 1542–1546), but this method has a high possibility of causing explosion during the reaction and nitrogen oxide which is a toxic gas is produced as a by-product after the reaction. The reaction using potassium permanganate as the oxidizing agent (*J. Chem. Soc.*, 1956, 4232–4237) requires treatment after the reaction using sulfuric acid, and the operation is dangerous and complex. A method is known in which chromic acid (*Helv. Chim. Acta*, 1948, 31, 422–426, *J. Am. Chem. Soc.*, 1967, 89, 6691-6695) or potassium superoxide (*Tetrahedron Lett.*, 1978, 3689–3690) is used as the oxidizing agent in the presence of sulfuric acid or perchloric acid, but there are problems in these reactions such as corrosiveness of the oxidizing agent and the use of an acid or a benzene solvent. It is hard to say that these methods for producing carboxylic acid from ketone are industrially superior methods because of the large load on the environment.

On the other hand, oxygen and hydrogen peroxide are excellent oxidizing agents in industrially applying them due to small environmental load, because they are inexpensive and have no corrosiveness, and there is no by-product after the reaction or it is harmless water.

Methods for producing carboxylic acid from ketone by using oxygen as the oxidizing agent are already known (*Chem. Ber.*, 1892, 25, 1271–1277, *Chem. Ber.*, 1892, 25, 2095–2102, *J. Chem. Soc.*, 1909, 95, 166–171, *J. Org. Chem.*, 1965, 30, 3768–3771), but large excess of a strong base based on the substrate is necessary in these methods. Also, formation of carboxylic acid from ketone by using oxygen as the oxidizing agent in the presence of a metal catalyst such as a manganese or cobalt salt has been reported (U.S. Pat. No. 2,005,183 specification, U.S. Pat. No. 2,316,548 specification, JP-A-13-213841, WOP 2001-87815 specification), but carboxylic acid is not obtained by these methods unless acetic acid is used at a solvent amount. In addition, when aerobic oxidation is carried out by using an iron or vanadium catalyst (*J. Org. Chem.*, 1983, 48, 1133–1135, *J. Org. Chem.*, 1993, 58, 5663–5665), the conversion ratio is low unless an electron donating substituent group is linked to the α-position of the ketone. Moreover, a benzene solvent is necessary for the reaction when the iron catalyst is used.

On the other hand, as a method for obtaining carboxylic acid by using hydrogen peroxide as the oxidizing agent, a method using a catalytic amount of a metal compound belonging to Group 3 or Group 13 of the Periodic Table has been proposed (WOP 2000-53593 specification), but the product obtained by this method is not carboxylic acid but an ester or lactone compound.

In addition, a method in which a homogeneous solution of cyclohexanone and hydrogen peroxide is prepared in advance by using a polar solvent, and adipic acid is produced by allowing this homogeneous solution to react in the presence of a catalyst such as of a metal oxide belonging to Group 6 of the Periodic Table has been proposed (JP-A-54-135720).

However, it cannot be said yet that the method is sufficient as an industrial carboxylic acid production method, because the yield of adipic acid by this method is considered to be merely about 50%, and it is essential to use a polar solvent such as acetic acid or t-butyl alcohol for preparing a homogeneous solution by dissolving cyclohexanone in an aqueous hydrogen peroxide, so that the reaction operation and apparatus become complex because of the necessity to employ a means for its removal at the time of the isolation of adipic acid as the product of interest, in addition to the indication on the influence and toxicity of the polar organic solvent itself upon the environment and human body.

DISCLOSURE OF THE INVENTION

The present invention has been made in order to solve the above-described problems involved in the related art, and its object is to provide a safe, convenient and efficient method for producing carboxylic acid by a reaction of alicyclic alcohol or alicyclic ketone with an aqueous hydrogen peroxide to thereby obtain carboxylic acid in high yield from alicyclic alcohol or alicyclic ketone under mild reaction conditions, wherein the reaction operation is simple and easy, a step for removing solvent after completion of the reaction is not necessary and influence and toxicity upon the environment and human body are markedly small.

In order to solve the above-described problems, the present inventors have conducted intensive studies and found as a result that, when a reaction using a heterogeneous solution system of an aqueous hydrogen peroxide with an oily alicyclic alcohol or an oily alicyclic ketone is selected instead of the conventional reaction method in which the oxidation reaction is carried out in a homogeneous solution system of an aqueous hydrogen peroxide with a polar solvent solution of alicyclic alcohol or alicyclic ketone, the corresponding carboxylic acid can be produced safely and conveniently in high yield which is different from the conventional common technical knowledge, thus resulting in the accomplishment of the present invention.

That is, according to the present invention, the following inventions are provided.

(1) A method for producing carboxylic acid, which comprises reacting an oily alicyclic alcohol or an oily alicyclic ketone with an aqueous hydrogen peroxide in the presence of a catalyst containing a metal compound belonging to Group 6 of the Periodic Table in a heterogeneous solution system.

(2) The method for producing carboxylic acid according to the above-described (1), wherein the metal compound belonging to Group 6 of the Periodic Table is a metal compound of at least one member selected from chromium, molybdenum and tungsten.

(3) The method for producing carboxylic acid according to the above-described (1) or (2), wherein the alicyclic alcohol is a compound represented by the following formula (1):

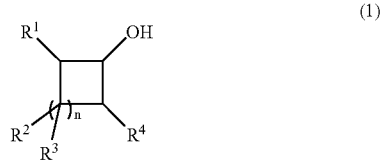

wherein n is an integer of 1 to 18; and $R^1$, $R^2$, $R^3$ and $R^4$ are the same or different and each represents a hydrogen atom, a hydroxyl group, a halogen atom, a carboxyl group, an alkyl group having from 1 to 4 carbon atoms, an alkoxy group having from 1 to 4 carbon atoms, a cycloalkyl group having from 3 to 7 carbon atoms, an aryl group, an aralkyl group, an acyl group or an acyloxy group, or $R^1$ and $R^2$, $R^1$ and $R^3$, $R^1$ and $R^4$, $R^2$ and $R^3$, $R^2$ and $R^4$ or $R^3$ and $R^4$ may be taken together to form a carbon ring which may be substituted with an alkyl group having from 1 to 4 carbon atoms, an alkoxy group having from 1 to 4 carbon atoms, a cycloalkyl group having from 3 to 7 carbon atoms, an aryl group, an aralkyl group, a carboxyl group or a halogen atom.

(4) The method for producing carboxylic acid according to the above-described (1) or (2), wherein the alicyclic ketone is a compound represented by the following formula (2):

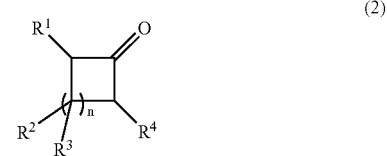

wherein n is an integer of 1 to 18; and $R^1$, $R^2$, $R^3$ and $R^4$ are the same or different and each represents a hydrogen atom, a hydroxyl group, a halogen atom, a carboxyl group, an alkyl group having from 1 to 4 carbon atoms, an alkoxy group having from 1 to 4 carbon atoms, a cycloalkyl group having from 3 to 7 carbon atoms, an aryl group, an aralkyl group, an acyl group or an acyloxy group, or $R^1$ and $R^2$, $R^1$ and $R^3$, $R^1$ and $R^4$, $R^2$ and $R^3$, $R^2$ and $R^4$ or $R^3$ and $R^4$ may be taken together to form a carbon ring which may be substituted with an alkyl group having from 1 to 4 carbon atoms, an alkoxy group having from 1 to 4 carbon atoms, a cycloalkyl group having from 3 to 7 carbon atoms, an aryl group, an aralkyl group, a carboxyl group or a halogen atom.

(5) The method for producing carboxylic acid according to any one of the above-described (1) to (4), wherein the carboxylic acid is glutaric acid or adipic acid.

BEST MODE FOR CARRYING OUT THE INVENTION

The method for producing carboxylic acid of the present invention based on the oxidation reaction of alicyclic alcohol or alicyclic ketone using hydrogen peroxide is characterized in that the oxidation reaction is carried out in a heterogeneous solution of an aqueous hydrogen peroxide and an oily alicyclic alcohol or an oily alicyclic ketone in the presence of a catalyst containing a metal compound belonging to Group 6 of the Periodic Table.

Conventionally, in a liquid-liquid reaction, when materials themselves or the materials and reaction reagents such as an oxidizing agent and a reaction accelerator do not have compatibility, it has been considered that a process in which a homogenous solution of the materials and a reaction reagent and the like is prepared in advance by using a solvent capable of mutually dissolving them for smooth reaction and then the reaction is carried out is advantageous from the points of selectivity, yield and the like.

As described above, this idea is also followed in the case of the carboxylic acid synthesis reaction through the reaction of alicyclic alcohol or alicyclic ketone with hydrogen peroxide, and a process in which a homogeneous solution of cyclohexanol or cyclohexanone and hydrogen peroxide is prepared in advance by using a polar solvent such as acetic acid or 1-butyl alcohol, and adipic acid is produced by allowing this homogeneous solution to react in the presence of a catalyst such as a metal oxide belonging to Group 6 of the Periodic Table has been employed in the invention described in JP-A-54-135720.

From the viewpoint of carrying out such an oxidation reaction more efficiently while taking protection of the environment and human body into consideration, the present inventors have carried out various studies and experiments and theoretical discussions and found as a result that, when this oxidation reaction of an aliphatic alcohol or aliphatic ketone is carried out using hydrogen peroxidase as the oxidizing agent in a heterogeneous solution system of an oily alicyclic alcohol or an alicyclic ketone and an aqueous hydrogen peroxide, different from the case of a homologous solution system like the conventional technical knowledge, yield of the carboxylic acid is markedly improved and it considerably contributes to the reduction of environmental load. Such a knowledge cannot be expected at all by the conventional technical common sense but is a specific phenomenon found for the first time by the present inventors through continuous efforts of experiments and studies.

The reason why the oxidation reaction in the heterogeneous solution system of the present invention leads to the sharp increase in the yield of carboxylic acid is not theoretically revealed yet, but it is considered that this is mainly caused because reduction of activity by the solvation of catalytic activity species does not occur in an oily solution, or the reaction is sharply accelerated in the water-oil phase interface for some reasons.

As the material used in the present invention, conventionally known general alicyclic alcohol or alicyclic ketone can be used without particular limitation, but as the galicyclic alcohol, the alicyclic alcohol represented by the following formula (1) can be preferably used.

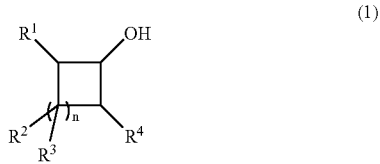

(1)

In the formula, n is an integer of 1 to 18; and $R^1$, $R^2$, $R^3$ and $R^4$ are the same or different and each represents a hydrogen atom, a hydroxyl group, a halogen atom, a carboxyl group, an alkyl group having from 1 to 4 carbon atoms, an alkoxy group having from 1 to 4 carbon atoms, a cycloalkyl group having from 3 to 7 carbon atoms, an aryl group, an aralkyl group, an acyl group or an acyloxy group, or $R^1$ and $R^2$, $R^1$ and $R^3$, $R^1$ and $R^4$, $R^2$ and $R^3$, $R^2$ and $R^4$ or $R^3$ and $R^4$ may be taken together to form a carbon ring which may be substituted with an alkyl group having from 1 to 4 carbon atoms, an alkoxy group having from 1 to 4 carbon atoms, a cycloalkyl group having from 3 to 7 carbon atoms, an aryl group, an aralkyl group, a carboxyl group or a halogen atom.

Examples of the alicyclic alcohol represented by formula (1) include cyclobutanol, cyclopentanol, cyclohexanol, cycloheptanol, cyclooctanol, cyclononanol, cyclodecanol, cycloundecanol, cyclododecanol, cyclotridecanol, cyclotetradecanol, cyclopentadecanol, cyclohexadecanol, cycloheptadecanol, cyclooctadecanol, cyclononadecanol, cycloicosanol, cycloheneicosanol, 1-methylcyclopentanol, 2-methylcyclopentanol, 1,2-dimethylcyclopentanol, 1,3-dimethylcyclopentanol, 1,4-dimethylcyclopentanol, 2,3-dimethylcyclopentanol, 1,2,3-trimethylcyclopentanol, 1,2,4-trimethylcyclopentanol, 1,2,3,4-tetramethylcyclopentanol, 1-methylcyclohexanol, 2-methylcyclohexanol, 3-methylcyclohexanol, 1,2-dimethylcyclohexanol, 1,3-dimethylcyclohexanol, 1,4-dimethylcyclohexanol, 1,5-dimethylcyclohexanol, 2,3-dimethylcyclohexanol, 2,4-dimethylcyclohexanol, 1,2,3-trimethylcyclohexanol, 1,2,4-trimethylcyclohexanol, 1,2,5-trimethylcyclohexanol, 1,3,4-trimethylcyclohexanol, 1,3,5-trimethylcyclohexanol, 2,3,4-trimethylcyclohexanol, 1,2,3,4-tetramethylcyclohexanol, 1,2,3,5-tetramethylcyclohexanol, 1,2,4,5-tetramethylcyclohexanol, 1,2,3,4,5-pentamethylcyclohexanol, 1-methylcycloheptanol, 1-methylcyclooctanol, 1-methylcyclononanol, 1-methylcyclodecanol, 1-methylcycloundecanol, 1-methylcyclododecanol, 1-methylcyclotridecanol, 1-methylcyclotetradecanol, 1-methylcyclopentadecanol, 1-methylcyclohexadecanol, 1-methylcycloheptadecanol, 1-methylcyclooctadecanol, 1-methylcyclononadecanol, 1-methylcycloicosanol, 1-methylcycloheneicosanol, 1-phenylcyclohexanol, 1-benzylcyclohexanol, 1,2-cyclohexanediol, 1-chlorocyclopentanol, 1-bromocyclopentanol, 1-chlorocyclohexanol, 1-bromocyclohexanol, cyclopentanol-1-carboxylic acid, cyclohexanol-1-carboxylic acid, 1-acetylcyclopentanol, 1-acetylcyclohexanol and the like. The alcohol preferably used in the present invention is cyclopentanol or cyclohexanol.

As the ketone used in the present invention, conventionally known general alicyclic ketone can be used without particular limitation, but the alicyclic ketone represented by the following formula (2) can be preferably used.

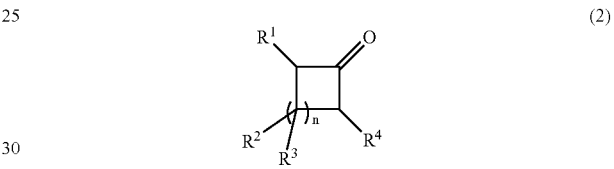

(2)

In the formula, n is an integer of 1 to 18; and $R^1$, $R^2$, $R^3$ and $R^4$ are the same or different and each represents a hydrogen atom, a hydroxyl group, a halogen atom, a carboxyl group, an alkyl group having from 1 to 4 carbon atoms, an alkoxy group having from 1 to 4 carbon atoms, a cycloalkyl group having from 3 to 7 carbon atoms, an aryl group, an aralkyl group, an acyl group or an acyloxy group, or $R^1$ and $R^2$, $R^1$ and $R^3$, $R^1$ and $R^4$, $R^2$ and $R^3$, $R^2$ and $R^4$ or $R^3$ and $R^4$ may be taken to form a carbon ring which may be substituted with an alkyl group having from 1 to 4 carbon atoms, an alkoxy group having from 1 to 4 carbon atoms, a cycloalkyl group having from 3 to 7 carbon atoms, an aryl group, an aralkyl group, a carboxyl group or a halogen atom.

Examples of the alicyclic alcohol represented by formula (1) include cyclobutanone, cyclopentanone, cyclohexanone, cycloheptanone, cyclooctanone, cyclononanone, cyclodecanone, cycloundecanone, cyclododecanone, cyclotridecanone, cyclotetradecanone, cyclopentadecanone, cyclohexadecanone, cycloheptadecanone, cyclooctadecanone, cyclononadecanone, cycloicosanone, cycloheneicosanone, 1-methylcyclopentanone, 2-methylcyclopentanone, 1,2-dimethylcyclopentanone, 1,3-dimethylcyclopentanone, 1,4-dimethylcyclopentanone, 2,3-dimethylcyclopentanone, 1,2,3-trimethylcyclopentanone, 1,2,4-trimethylcyclopentanone, 1,2,3,4-tetramethylcyclopentanone, 1-methylcyclohexanone, 2-methylcyclohexanone, 3-methylcyclohexanone, 1,2-dimethylcyclohexanone, 1,3-dimethylcyclohexanone, 1,4-dimethylcyclohexanone, 1,5-dimethylcyclohexanone, 2,3-dimethylcyclohexanone, 2,4-dimethylcyclohexanone, 1,2,3-trimethylcyclohexanone, 1,2,4-trimethylcyclohexanone, 1,2,5-trimethylcyclohexanone, 1,3,4-trimethylcyclohexanone, 1,3,5-trimethylcyclohexanone, 2,3,4-trimethylcyclohexanone, 1,2,3,4-tetramethylcyclohexanone, 1,2,3,5-tetramethylcyclohexanone, 1,2,4,5-tetramethylcyclohexanone, 1,2,3,4,5- pentamethylcyclohexanone, 1-methylcycloheptanone, 1-methylcyclooctanone, 1-methylcyclononanone, 1-methylcyclodecanone, 1-methylcycloundecanone, 1-methylcyclododecanone, 1-methylcyclotridecanone, 1-methylcyclotetradecanone, 1-methylcyclopentadecanone, 1-methylcyclohexadecanone, 1-methylcycloheptadecanone, 1-methylcyclooctadecanone, 1-methylcyclononadecanone, 1-methylcycloicosanone, 1-methylcycloheneicosanone, 1-phenylcyclohexanone, 1-benzylcyclohexanone, 1-hydroxycyclohexanone, 1,2-cyclohexanedione, 1-chlorocyclopentanone, 1-bromocyclopentanone, 1-chlorocyclohexanone, 1-bromocyclohexanone, cyclopentanone-1-carboxylic acid, cyclohexanone-1-carboxylic acid, 1-acetylcyclopentanone, 1-acetylcyclohexanone and the like. The ketone preferably used in the present invention is cyclopentenone, cyclohexanone, cycloheptanone, cyclooctanone or the like.

According to the present invention, as described above, its object is to provide a safe, convenient and efficient method for producing carboxylic acid by a reaction of alicyclic alcohol or alicyclic ketone with an aqueous hydrogen peroxide to thereby obtain carboxylic acid in high yield from alicyclic alcohol or alicyclic ketone under mild reaction conditions, wherein the reaction operation is simple and easy, a step for removing solvent after completion of the reaction is not necessary and influence and toxicity upon the environment and human body are markedly small, so that it is extremely important that the above-described oxidation reaction is carried out in a heterogeneous solution system without using an organic solvent as far as possible.

Accordingly, if possible, the above-described alicyclic alcohol or alicyclic ketone is used as an oily solution of itself such that its phase is separated from an aqueous hydrogen peroxide phase which is the oxidizing agent.

The oily alicyclic alcohol or alicyclic ketone includes an oily solvent solution of alicyclic alcohol or alicyclic ketone prepared by dissolving it in a non-polar solvent having no compatibility with water such as hydrocarbon, in addition to an oily alicyclic alcohol or alicyclic ketone by itself, but it is most preferable to use an oily alicyclic alcohol or alicyclic ketone by itself in view of the above-described environmental load reduction and solvent removing operation.

The oxidizing agent used in the method of the present invention is hydrogen peroxide, and the hydrogen peroxide is used in the form of an aqueous solution in carrying out the method. The concentration of the aqueous hydrogen peroxide is not particularly limited, because the oxidation reaction of alicyclic alcohol or alicyclic ketone proceeds in response to its concentration, but it is selected within the range of usually 1 to 80% by weight, preferably 30 to 60% by weight. In addition, the amount of the aqueous hydrogen peroxide is not limited too, but it is selected within the range of usually 3.0 to 30.0 equivalents, preferably 3.3 to 8.0 equivalents, based on the alicyclic alcohol.

The catalyst used in the method of the present invention mainly comprises a metal compound belonging to Group 6 of the Periodic Table. The metal compound includes a metal compound of at least one member selected from chromium, molybdenum and tungsten.

Specifically, examples of the chromium compound include a chromium compound which forms a chromic acid anion in water, such as chromic acid, chromium trioxide, chromium trisulfide, chromium hexachloride, phosphorus chromate, ammonium chromate, potassium chromate dihydrate, sodium chromate dihydrate and the like, and chromic acid, chromium trioxide and phosphorus chromate are preferable.

Examples of the molybdenum compound include a molybdenum compound which forms a molybdic acid anion in water, such as molybdic acid, molybdenum trioxide, molybdenum trisulfide, molybdenum hexachloride, phosphorus molybdate, ammonium molybdate, potassium molybdate dihydrate, sodium molybdate dihydrate and the like, and molybdic acid, molybdenum trioxide and phosphorus molybdate are preferable.

Examples of the tungsten compound include a tungsten compound which forms a tungstic acid anion in water, such as tungstic acid, tungsten trioxide tungsten trisulfide, tungsten hexachloride, phosphorus tungstate, ammonium tungstate, potassium tungstate dihydrate, sodium tungstate dihydrate and the like, and tungstic acid, tungsten trioxide and phosphorus tungstate are preferable.

These metal compounds belonging to Group 6 of the Periodic Table may be used alone or as a mixture of two or more. In addition, the used amount is not particularly limited, but it is selected from the range of usually 0.0001 to 20% by mol, preferably 0.01 to 10% by mol, based on the material alicyclic alcohol or alicyclic ketone.

Although the catalyst to be used in the production method of the present invention mainly comprises a metal compound belonging to Group 6 of the Periodic Table, it is possible to use an auxiliary catalyst and the like, such as phosphoric acid, if necessary.

Reaction conditions of the method of the present invention are not particularly limited, but the reaction is carried out within the range of usually 30 to 120° C., preferably 50 to 100° C. The reaction pressure may be any of ordinary pressure, pressurization and reduced pressure, but it is preferable to carry out under ordinary pressure.

In addition, according to the production method of the present invention, added order of the material, oxidizing agent and catalyst and the reaction mode are not particularly limited, so long as it is a method in which an aqueous hydrogen peroxide and alicyclic alcohol or alicyclic ketone form a heterogeneous solution in the reaction system, but in general, a method is employed in which alicyclic alcohol or alicyclic ketone is added to an aqueous hydrogen peroxide mixed with a catalyst to thereby form their heterogeneous mixture in advance, and then they are allowed to react under stirring.

According to the production method of the present invention, for example, carboxylic acid such as glutaric acid or adipic acid can be obtained in high yield from its corresponding alicyclic alcohol by employing the above-described characteristic oxidation reaction process.

Specifically, dicarboxylic acid represented by the following formula (3):

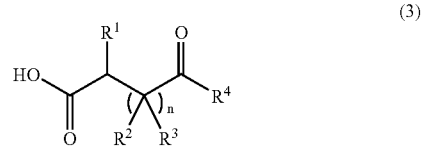

(3)

(in the formula, n, $R^1$, $R^2$ and $R^3$ have the same meanings as defined above) can be obtained from alcohol in which the $R^4$ in the above-described alicyclic alcohol of formula (1) or the above-described formula (2) is a hydrogen atom, a hydroxyl group or a halogen atom.

Also, when the $R^4$ in the above-described alicyclic alcohol of formula (1) or the above-described alicyclic ketone of formula (2) is a group other than a hydrogen atom, a hydroxyl group or a halogen atom, it is possible to obtain keto-carboxylic acid represented by the following formula (4):

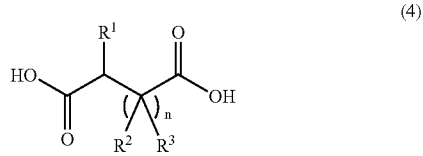

(in the formula, n, $R^1$, $R^2$ and $R^3$ have the same meanings as defined above; and $R^4$ represents a carboxyl group, an alkyl group having from 1 to 4 carbon atoms, an alkoxy group having from 1 to 4 carbon atoms, a cycloalkyl group having from 3 to 7 carbon atoms, an aryl group, an aralkyl group, an acyl group or an acyloxy group, which are the same or different, and $R^1$ and $R^2$, $R^1$ and $R^3$, $R^1$ and $R^4$, $R^2$ and $R^3$, $R^2$ and $R^4$ or $R^3$ and $R^4$ may be taken together to form a carbon ring which may be substituted with an alkyl group having from 1 to 4 carbon atoms, an alkoxy group having from 1 to 4 carbon atoms, a cycloalkyl group having from 3 to 7 carbon atoms, an aryl group, an aralkyl group, a carboxyl group or a halogen atom).

Examples of the carboxylic acid which can be obtained by the method of the present invention include succinic acid, glutaric acid, adipic acid, pimelic acid, suberic acid, azelaic acid, sebacic acid, undecanedioic acid, brassylic acid, tridecanedioic acid, tetradecanedioic acid, pentadecanedioic acid, hexadecanedioic acid, heptadecanedioic acid, octadecanedioic acid, nonadecanedioic acid, icosanedioic acid, heneicosanedionic acid, 5-oxohexanoic acid, 2-methylglutaric acid, 4-methyl-5-oxohexanoic acid, 3-methyl-5-oxohexanoic acid, 2-methyl-5-oxohexanoic acid, 2,3-dimethylglutaric acid, 3,4-dimethyl-5-oxohexanoic acid, 2,4-dimethyl-5-oxohexanoic acid, 2,3-dimethyl-5-oxohexanoic acid, 2,3,4-trimethyl-5-oxohexanoic acid, 6-oxoheptanoic acid, 2-methyladipic acid, 3-methyladipic acid, 5-methyl-6-oxoheptanoic acid, 4-methyl-6-oxoheptanoic acid, 3n-methyl-6-oxoheptanoic acid, 2-methyl-6-oxoheptanoic acid, 2,3-dimethyladipic acid, 2,4-dimethyladipic acid, 4,5-dimethyl-6-oxoheptanoic acid, 3,5-dimethyl-6-oxoheptanoic acid, 2,5-dimethyl-6-oxoheptanoic acid, 2,3-dimethyl-6-oxoheptanoic acid, 3,4-dimethyl-6-oxoheptanoic acid, 2,4-dimethyl-6-oxoheptanoic acid, 2,3,4-trimethyladipic acid, 3,4,5-trimethyl-6-oxoheptanoic acid, 2,4,5-trimethyl-6-oxoheptanoic acid, 2,3,4-trimethyl-6-oxoheptanoic acid, 2,3,5-trimethyl-6-oxoheptanoic acid, 2,3,4,5-tetramethyl-6-oxoheptanoic acid, 7-oxooctanoic acid, 8-oxononanoic acid, 9-oxodecanoic acid, 10-oxoundecanoic acid, 11-oxododecanoic acid, 12-oxotridecanoic acid, 13-oxotetradecanoic acid, 14-oxopentadecanoic acid, 15-oxohexadecanoic acid, 16-oxoheptadecanoic acid, 17-oxooctadecanoic acid, 18-oxononadecanoic acid, 19-oxoicosanoic acid, 20-oxoheneicosanoic acid, 21-oxodocosanoic acid, 6-phenyl-6-oxohexanoic acid, 7-phenyl-6-oxoheptanoic acid and the like. Among these, glutaric acid and adipic acid are preferably synthesized.

According to the method of the present invention, the carboxylic acid of interest can be obtained in high yield and high selectivity after completion of the above-described reaction, by concentrating the mixed solution containing the formed carboxylic acid and then separating and purifying the product by usual methods such as recrystallization, distillation, and sublimation.

EXAMPLES

The present invention is described below in detail based on the following Examples; however, the present invention is not limited to these Examples.

Example 1

$H_2WO_4$ (25.0 mg, 0.100 mmol), 30% aqueous hydrogen peroxide (5.1 ml, 44 mmol) and cyclopentanol (0.91 ml, 10 mmol) were mixed and stirred at 90° C. for 20 hours. After completion of the reaction, the mixture was cooled to room temperature. After methylation with trimethylsilyl diazomethane, the yield of glutaric acid was determined by GLC using biphenyl as the internal standard to find that it was 91%.

Example 2

$H_2WO_4$ (25.0 mg, 0.100 mmol), 30% aqueous hydrogen peroxide (5.1 ml, 44 mmol) and cyclohexanol (1.06 ml, 10 mmol) were mixed and stirred at 90° C. for 20 hours. After completion of the reaction, this was cooled to room temperature. When determination by GLC was carried out in the same manner as in Example 1, the yield of adipic acid was 89%.

Example 3

$H_2WO_4$ (2.50 g, 0.010 mol), 30% aqueous hydrogen peroxide (510 ml, 4.4 mol) and cyclohexanol (101 ml, 1.0 mol) were mixed and stirred at 90° C. for 20 hours. When the mixture was allowed to stand overnight at 0° C., white crystals were precipitated. The thus obtained crystals were collected by filtration under a reduced pressure and washed with cold water (20 ml). After confirming that the filtrate does not show peroxide reaction by using potassium iodide starch paper, vacuum drying was carried out. White crystals of adipic acid were obtained in yield of 85% (125 g, 0.85 mol).

Example 4

$H_2WO_4$ (25.0 mg, 0.100 mmol), 30% aqueous hydrogen peroxide (3.7 ml, 33 mmol) and cyclopentanone (1.0 ml, 10 mmol) were mixed and stirred at 90° C. for 20 hours. After completion of the reaction, the mixture was cooled to room temperature. After methylation with trimethylsilyl diazomethane, the yield of glutaric acid was determined by GLC using biphenyl as the internal standard to find that it was 98%.

Example 5

$H_2WO_4$ (25.0 mg, 0.100 mmol), 30% aqueous hydrogen peroxide (5.1 ml, 44 mmol) and cyclohexanone (1.0 ml, 10 mmol) were mixed and stirred at 90° C. for 20 hours. When determination by GLC was carried out in the same manner as in Example 1, the yield of adipic acid was 99%.

Example 6

H₂WO₄ (2.50 g, 0.010 mol), 30% aqueous hydrogen peroxide (370 ml, 3.3 mol) and cyclohexanone (100 ml, 0.966 mol) were mixed and stirred at 90° C. for 20 hours. When the mixture was allowed to stand overnight at 0° C., white crystals were precipitated. The thus obtained crystals were collected by filtration under a reduced pressure and washed with cold water (20 ml). After confirming that the filtrate does not show peroxide reaction by using potassium iodide starch paper, vacuum drying was carried out. White crystals of adipic acid were obtained with a yield of 92% (130 g, 0.899 mol).

Example 7

H₂WO₄ (25.0 mg, 0.100 mmol), 30% aqueous hydrogen peroxide (3.7 ml, 33 mmol) and cycloheptanone (1.2 ml, 10 mmol) were mixed and stirred at 90° C. for 20 hours. When determination by GLC was carried out in the same manner as in Example 1, the yield of pimelic acid was 81%.

Example 8

H₂WO₄ (25.0 mg, 0.100 mmol), 30% aqueous hydrogen peroxide (3.7 ml, 33 mmol) and cyclooctanone (1.3 ml, 10 mmol) were mixed and stirred at 90° C. for 20 hours. When determination by GLC was carried out in the same manner as in Example 1, the yield of suberic acid was 85%.

Comparative Example 1

An oxidation reaction in a homogenous solution was carried out in the same manner as in Example 2 by using a cyclohexanol (1.06 ml, 10 mmol) solution dissolved in t-butyl alcohol (3 ml) instead of cyclohexanol in Example 2, and determination by GLC was carried out to find that the yield of adipic acid was 52%.

Comparative Example 2

An oxidation reaction in a homogenous solution was carried out in the same manner as in Example 2 by using a cyclohexanone (1.0 ml, 10 mmol) solution dissolved in t-butyl alcohol (3 ml) instead of the cyclohexanone in Example 5, and determination by GLC was carried out to find that the yield of adipic acid was 52%.

INDUSTRIAL APPLICABILITY

According to the method of the present invention, carboxylic acid such as glutaric acid or adipic acid which is an important intermediate in the synthesis of diesters, polyesters and polyamides which are useful substances broadly used in various industrial fields, including chemical industry, as plasticizers, lubricants, heating media, dielectric media, fibers, copolymers, paint resins, surface active agents, fungicides, insecticides, adhesives and the like, can be obtained under mild reaction conditions and in high yield.

In addition, since the method of the present invention does not use an organic solvent, an acid and a base, the reaction operation is simple and easy, a solvent removing step or the like after completion of the reaction is not necessary, influence and toxicity upon the environment and human body are markedly small and it also has the effect to reduce load on the environment, so that carboxylic acid can be produced safely, conveniently and efficiently.

Thus, it can be said that the method of the present invention is an invention which produces industrially great effects.

The invention claimed is:

1. A method for producing carboxylic acid, which comprises reacting an oily alicyclic alcohol or an oily alicyclic ketone with an aqueous hydrogen peroxide in the presence of a catalyst containing a metal compound belonging to Group 6 of the Periodic Table in a heterogeneous solution system.

2. The method for producing carboxylic acid according to claim 1, wherein the metal compound belonging to Group 6 of the Periodic Table is a metal compound of at least one member selected from chromium, molybdenum and tungsten.

3. The method for producing carboxylic acid according to claim 1, wherein the alicyclic alcohol is a compound represented by the following formula (1):

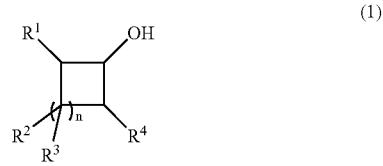

(1)

wherein n is an integer of 1 to 18; and $R^1$, $R^2$, $R^3$ and $R^4$ are the same or different and each represents a hydrogen atom, a hydroxyl group, a halogen atom, a carboxyl group, an alkyl group having from 1 to 4 carbon atoms, an alkoxy group having from 1 to 4 carbon atoms, a cycloalkyl group having from 3 to 7 carbon atoms, an aryl group, an aralkyl group, an acyl group or an acyloxy group, or $R^1$ and $R^2$, $R^1$ and $R^3$, $R^1$ and $R^4$, $R^2$ and $R^3$, $R^2$ and $R^4$ or $R^3$ and $R^4$ may be taken together to form a carbon ring which may be substituted with an alkyl group having from 1 to 4 carbon atoms, an alkoxy group having from 1 to 4 carbon atoms, a cycloalkyl group having from 3 to 7 carbon atoms, an aryl group, an aralkyl group, a carboxyl group or a halogen atom.

4. The method for producing carboxylic acid according to claim 1, wherein the alicyclic ketone is a compound represented by the following formula (2)

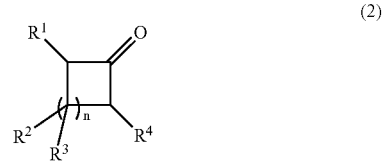

(2)

wherein n is an integer of 1 to 18; and $R^1$, $R^2$, $R^3$ and $R^4$ are the same or different and each represents a hydrogen atom, a hydroxyl group, a halogen atom, a carboxyl group, an alkyl group having from 1 to 4 carbon atoms, an alkoxy group having from 1 to 4 carbon atoms, a cycloalkyl group having from 3 to 7 carbon atoms, an aryl group, an aralkyl group, an acyl group or an acyloxy group, or $R^1$ and $R^2$, $R^1$ and $R^3$, $R^1$ and $R^4$, $R^2$ and $R^3$, $R^2$ and $R^4$ or $R^3$ and $R^4$ may be taken together to form a carbon ring which may be substituted with an alkyl group having from 1 to 4 carbon atoms, an alkoxy group having from 1 to 4 carbon atoms, a cycloalkyl group having from 3 to 7 carbon atoms, an aryl group, an aralkyl group, a carboxyl group or a halogen atom.

5. The method for producing carboxylic acid according to claim 1, wherein the carboxylic acid is glutaric acid, adipic acid, pimelic acid, or suberic acid.

* * * * *